US006607734B1

(12) United States Patent
Afriat

(10) Patent No.: US 6,607,734 B1
(45) Date of Patent: Aug. 19, 2003

(54) COMPOSITION IN THE FORM OF A WATER-IN-OIL EMULSION CONTAINING FIBERS, AND COSMETIC USE THEREOF

(75) Inventor: Isabelle Afriat, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/688,118

(22) Filed: Oct. 16, 2000

(30) Foreign Application Priority Data

Oct. 15, 1999 (FR) .......................................... 99 12910

(51) Int. Cl.[7] .......................... A61K 6/00; A61K 7/00; A61K 7/06; A61K 7/11; A61K 31/74; A61K 31/695; A01N 55/00; A01N 25/00

(52) U.S. Cl. ................ 424/401; 424/78.03; 424/70.12; 514/63; 514/844; 514/937

(58) Field of Search ............................ 424/401, 78.02, 424/78.03, 70.1, 70.12; 514/63, 844, 937

(56) References Cited

U.S. PATENT DOCUMENTS

| | | | | | |
|---|---|---|---|---|---|
| 4,659,562 | A | | 4/1987 | Arraudeau et al. | 424/63 |
| 4,720,353 | A | * | 1/1988 | Bell | 516/23 |
| 5,015,469 | A | * | 5/1991 | Yoneyama et al. | 424/59 |
| 5,250,289 | A | | 10/1993 | Boothroyd et al. | |
| 5,362,482 | A | | 11/1994 | Yoneyama et al. | |
| 5,498,407 | A | | 3/1996 | Atlas | |
| 5,523,091 | A | | 6/1996 | Pastour et al. | |
| 5,578,641 | A | * | 11/1996 | Jackson et al. | 514/547 |
| 5,665,368 | A | * | 9/1997 | Lentini et al. | 424/401 |
| 5,777,091 | A | * | 7/1998 | Kuhn et al. | 536/20 |
| 5,851,539 | A | | 12/1998 | Mellul et al. | |
| 5,863,544 | A | | 1/1999 | Wilcox et al. | |
| 5,871,762 | A | * | 2/1999 | Venkitaraman et al. | 424/402 |
| 5,902,591 | A | * | 5/1999 | Herstein | 424/40 |
| 5,935,589 | A | | 8/1999 | Mukherjee et al. | |
| 5,939,054 | A | | 8/1999 | Msika et al. | |
| 5,942,213 | A | | 8/1999 | Bara et al. | |
| 5,961,998 | A | | 10/1999 | Arnaud et al. | |
| 5,965,146 | A | | 10/1999 | Franzke et al. | |
| 5,972,315 | A | | 10/1999 | Voss et al. | |
| 6,015,548 | A | | 1/2000 | Siddiqui et al. | |
| 6,051,211 | A | | 4/2000 | Hansenne et al. | |
| 6,106,818 | A | * | 8/2000 | Dulog et al. | 424/78.03 |
| 6,190,678 | B1 | | 2/2001 | Hasenoehri et al. | |
| 6,264,881 | B1 | | 7/2001 | Plee et al. | |

FOREIGN PATENT DOCUMENTS

| | | |
|---|---|---|
| EP | 0 152 953 A2 | 8/1985 |
| EP | 0 268 164 | 5/1988 |
| EP | 0 336 900 A | 10/1989 |
| EP | 0 838 210 A2 | 4/1998 |
| EP | 10287523 | 10/1998 |
| FR | 7-196440 | 8/1995 |
| JP | 7196440 A | 8/1995 |
| WO | 98/50005 | 11/1998 |

OTHER PUBLICATIONS

Concise Encyclopedia of Chemistry, 1994, p. 651.

Hawley's Condensed Chemical Dictionary, 1997, p. 753.

Patent Abstracts of Japan, Publication No. 10287523, Oct. 27, 1998, "Cosmetic for Eyebrow" (English abstract only).

Patent Abstracts of Japan, Publication No. 62238211, Oct. 19, 1987, "Cosmetic for Skin Care" (English abstract only).

* cited by examiner

*Primary Examiner*—Sreeni Padmanabhan
*Assistant Examiner*—Lauren Q. Wells
(74) *Attorney, Agent, or Firm*—Oblon, Spivak, McClelland, Maier & Neustadt, P.C.

(57) ABSTRACT

A composition in the form of a water-in-oil emulsion containing fibers, at least one silicone surfactant and at least one clay. The composition may be used, for example, for caring for, treating, making up or cleansing the skin, the lips, the eyelashes and/or the hair.

21 Claims, No Drawings

COMPOSITION IN THE FORM OF A WATER-IN-OIL EMULSION CONTAINING FIBERS, AND COSMETIC USE THEREOF

BACKGROUND OF THE INVENTION

1. Field of the Invention

The present invention relates to a composition in the form of a water-in-oil (W/O) emulsion containing fibers, a silicone surfactant and a clay, and to the use of the composition, in particular for caring for, treating and/or making up body or facial skin, the hair, the eyelashes and/or the lips.

2. Background of the Invention

JP 07-196 440 discloses cosmetic compositions containing short polyamide fibers which give the compositions a velvety feel and good cosmetic behavior. However, the W/O emulsions described in that document, and for example in Examples 4 and 5, have a limited stability over time which is insufficient for a cosmetic product. In addition, the emulsion of Example 4 has a greasy feel.

Accordingly, there is still a need for W/O emulsions containing fibers, which are stable while at the same time having good cosmetic properties and thus not having the drawbacks of those of known compositions.

SUMMARY OF THE INVENTION

The Inventor has discovered, unexpectedly, that a combination of a silicone surfactant and a clay provides water-in-oil emulsions containing fibers, which are stable and cosmetically pleasant, i.e. soft and non-greasy. In addition, a larger amount of fibers can be incorporated into the compositions according to the invention as compared to the composition described in JP 07-196 440.

Accordingly, the present invention provides a composition in the form of an emulsion comprising, in a physiologically acceptable medium, an aqueous phase dispersed in an oily phase, and also fibers, at least one silicone surfactant and at least one clay.

The present invention provides a method of making the composition described above by combining water, at least one oil, at least one silicone surfactant and at least one clay.

The present invention provides a method of treating, protecting, caring for, removing make-up from and/or cleansing the skin, the lips and/or the hair, and/or for making up the skin and/or the lips, comprising applying the composition of the invention to skin, the lips and/or hair.

The present invention provides a method for the cosmetic treatment of the skin, hair and/or lips, comprising applying the composition of the invention to the skin, hair and/or lips.

A more complete appreciation of the invention and many of the attendant advantages thereof will be readily obtained as the same becomes better understood by reference to the following detailed description.

DETAILED DESCRIPTION OF THE INVENTION

The term "physiologically acceptable medium" refers to a medium which is compatible with the skin, the lips, the nails, the scalp and/or the hair.

The composition obtained according to the invention has good stability over time, even at a temperature above room temperature (for example 45° C.).

This composition has the appearance of a cream (supple product as opposed to a solid product) and it has a velvety texture which feels pleasant when applied.

The fibers which can be used in the composition of the invention can be fibers of synthetic or natural, and inorganic or organic origin. They can be short or long, individual or organized, for example in bundles. They can have any shape, and in particular a circular or polygonal (square, hexagonal or octagonal) cross section depending on the specific application envisaged. In particular, they have blunt and/or rounded ends to prevent injury.

In particular, the fibers have a length ranging from 1 nm to 20 mm, preferably from 10 nm to 5 mm and better still from 0.1 mm to 1.5 mm. These ranges for the length of the fibers include all specific values and subranges therebetween, such as 5 nm, 25 nm, 50 nm, 0.05 mm, 0.2 mm, 0.5 mm, 1 mm, 2 mm, 10 mm and 15 mm. Their cross section can be within a circle of diameter ranging from 2 nm to 100 $\mu$m, preferably ranging from 20 nm to 20 $\mu$m and better still from 5 $\mu$m to 50 $\mu$m. These ranges for the cross sections of the fibers include all specific values and subranges therebetween, such as 5 nm, 10 nm, 50 nm, 1 $\mu$m, 2 $\mu$m, 10 $\mu$m, 25 $\mu$m and 50 $\mu$m. The weight of the fibers is often given in denier or decitex.

The fibers can be those used in the manufacture of textiles, and in particular silk, cotton, wool or flax fibers, cellulose fibers extracted in particular from wood, plants or algae, polyamide (Nylon®), rayon or viscose fibers, acetate fibers, in particular rayon acetate, cellulose acetate or silk acetate fibers, poly-p-phenylene terephthamide fibers, in particular Kevlar® fibers, acrylic fibers, in particular polymethyl methacrylate or poly-2-hydroxyethyl methacrylate fibers, polyolefin fibers and in particular polyethylene or polypropylene fibers, glass, silica or aramid fibers, carbon fibers, in particular in graphite form, Teflon®, insoluble collagen, polyester, polyvinyl chloride or polyvinylidene chloride, polyvinyl alcohol, polyacrylonitrile, chitosan, polyurethane or polyethylene phthalate fibers, fibers formed from a mixture of polymers such as those mentioned above, for instance polyamide/polyester fibers, and mixtures of these fibers.

It is also possible to use surgical fibers, such as resorbable synthetic fibers prepared from glycolic acid and from caprolactone ("Monocryl" from Johnson & Johnson), resorbable synthetic fibers such as the copolymer of lactic acid and of glycolic acid ("Vicryl" from Johnson & Johnson), terephthalic polyester fibers ("Ethibond"from Johnson & Johnson) and stainless steel threads ("Steel" from Johnson & Johnson).

Moreover, the fibers may or may not be surface-treated and may or may not be coated. As coated fibers which can be used in the invention, mention may be made of polyamide fibers coated with copper sulphide for an antistatic effect (for example the R-STAT fibers from Rhodia) or another polymer allowing a particular organization of the fibers (specific surface treatment) or a surface treatment which induces color/hologram effects ("Lurex" fiber from Sildorex, for example).

The fibers which can be used in the composition according to the invention are preferably polyamide or poly-p-phenylene terephthamide fibers. Their length can range from 0.1 to 5 mm, preferably from 0.25 to 1.6 mm, and their average diameter can range from 5 to 50 $\mu$m. In particular, the polyamide fibers sold by Etablissements P. Bonte under the name Polyamide 0.9 Dtex 0.3 mm, having an average diameter of 6 $\mu$m, a weight of about 0.9 dtex and a length ranging from 0.3 mm to 1.5 mm, can be used. Poly-p-phenylene terephthamide fibers with an average diameter of 12 $\mu$m and a length of about 1.5 mm can also be used, such as those sold under the name Kevlar Floc by Du Pont Fibres.

The fibers can be present in the composition according to the invention in an amount ranging from 0.1 to 20% by weight and preferably from 0.5 to 12% by weight relative to the total weight of the composition. These ranges include all specific values and subranges therebetween, such as 0.2, 0.8, 1, 1.5, 2, 2.5, 3, 4, 5, 10 and 12% by weight relative to the total weight of the composition.

As silicone surfactants which may form part of the composition according to the invention, mention may be made of dimethicone copolyols and alkyldimethicone copolyols. Dimethicone copolyols which may be mentioned, for example, are the mixture of dimethicone copolyol, cyclomethicone and water (10/88/2) sold by Dow Coming under the name DC3225C or DC2-5225C, and the mixture of dimethicone copolyol and cyclopentasiloxane (85/15) sold under the name Abil EM-97 by Goldschmidt. Alkyldimethicone copolyols which may be mentioned in particular are those having an alkyl radical containing from 10 to 22 carbon atoms, such as cetyl dimethicone copolyol, for instance the product sold under the name Abil EM-90 by Goldschmidt; lauryl dimethicone copolyol and, for example, the mixture of about 91 % lauryl dimethicone copolyol and about 9% isostearyl alcohol, sold under the name Q2-5200 by Dow Coming, and mixtures of these silicone surfactants. The silicone surfactant is preferably a dimethicone copolyol.

The amount of silicone surfactant(s) in the composition of the invention preferably ranges from 0.1 to 5% by weight of active material, and better still from 0.5 to 2% by weight of active material, relative to the total weight of the composition. These ranges include all specific values and subranges therebetween, such as 0.2, 1, 1.5, 3 and 4 % by weight relative to the total weight of the composition.

As examples of clays which can be used in the composition of the invention, mention may be made of clays-of the kaolinite family, such as kaolinite, dickite or nacrite, and clays of the halloysite, dombassite, antigorite, benthierine, pyrophyllite, montmorillonite, beidellite, vermiculite, talc, stevensite, optionally modified hectorite (smectite), saponite, chlorite or sepiolite family.

The clays can also be chemically modified with various compounds such as acrylic acids, polysaccharides (for example carboxymethylcellulose) or organic cations.

According to one particularly preferred embodiment of the present invention, the clay used is chosen from kaolinite, montmorillonites and hectorites and mixtures thereof. The clay even more particularly used is a modified hectorite, and for example a bentone such as the mixture "cyclomethicone, Quaternium-18 hectorite, SD alcohol 40" (10/85/5) (CTFA name) sold under the name Bentone Gel VS-5 by Rheox.

The amount of clay(s) in the composition of the invention generally ranges from 0.1 to 10% by weight, particularly from 0.2 to 5% by weight and even more preferably from 0.3 to 1% by weight, relative to the total weight of the composition. These ranges include all specific values and subranges therebetween, such as 0.5, 1.5, 2, 3 and 8% by weight relative to the total weight of the composition.

The oily phase of the composition according to the invention can contain oils and fatty substances of any kind that are well known to those skilled in the art, for example oils of plant origin (jojoba, avocado, sesame, sunflower, corn, soybean, safflower or grape seed oil), mineral oils (petroleum jelly or optionally hydrogenated isoparaffins), synthetic oils (isopropyl myristate, cetearyl octanoate, polyisobutylene, ethylhexyl palpitate or alkyl benzoates), volatile or non-volatile silicone oils and fluoro or fluorosilicone oils, as well as mixtures of these oils.

Preferably, the oily phase of the composition of the invention comprises at least one silicone oil which can be present in an amount ranging, for example, from 5 to 50% by weight and preferably from 9 to 30% by weight relative to the total weight of the composition. These ranges for the amount of silicone oil include all specific values and subranges therebetween, such as 10, 20, 25 and 40% by weight relative to the total weight of the composition. Silicone oils which may be mentioned, for example, are volatile silicone oils such as cyclodimethylsiloxanes or cyclomethicones, for instance pentacyclomethicone, tetracyclomethicone or hexacyclomethicone; non-volatile silicone oils such as polydimethylsiloxanes (PDMS). The composition of the invention preferably contains at least one volatile silicone oil.

The oily phase can also contain other fatty constituents such as fatty alcohols, for instance stearyl alcohol, cetyl alcohol or cetearyl alcohol, fatty acids, gums, for example silicone gums, for instance the mixture PEWS containing $\alpha,\omega$-hydroxyl groups/PDMS 5 cst (12/88) sold under the name DC 1503 by the company Dow Corning, and lipophilic gelling agents such as bentone.

The oily phase is present in the composition according to the invention in an amount generally ranging from 10 to 50% and preferably from 12 to 40% by weight relative to the total weight of the composition, this amount comprising the amount of silicone surfactant. These ranges for the amount of oily phase include all specific values and subranges therebetween, such as 15, 20, 25, 30 and 45% by weight relative to the total weight of the composition.

The aqueous phase of the composition of the invention can range from 30 to 85% by weight and preferably from 40 to 75% by weight relative to the total weight of the composition, and can contain, besides water, solvents such as primary alcohols containing from 1 to 4 carbon atoms, such as ethanol, or polyols such as butylene glycol. These ranges for the amount of aqueous phase include all specific values and subranges therebetween, such as 35, 45, 50, 60, 70 and 80% by weight relative to the total weight of the composition. The solvent(s) can be present in an amount ranging from 0.1 to 30% by weight relative to the total weight of the composition. This range for the amount of solvent includes all specific values and subranges therebetween, such as 0.2, 0.5, 1, 2, 5, 10, 20 and 25% by weight relative to the total weight of the composition.

The composition of the invention can also contain lipophilic gelling agents such as elastomeric polyorganosiloxanes such as, for example, those sold under the names KSG 6 from Shin-Etsu, Trefil E-505C or Trefil E-506C from Dow Corning, Gransil (SR-CYC, SR DMF10, SR-DC556) from Grant Industries, or those sold in the form of preconstituted gels: KSG 15, KSG 17, KSG 16 and KSG 18 from Shin-Etsu, Gransil SR 5CYC gel, Gransil SR DMF 10 gel and Gransil SR DC556 gel from Grant Industries, 1229-02-167 and 1229-02-168 from General Electric. A mixture of these commercial products can also be used.

The composition according to the invention is in the form of a cream and can in particular constitute a cosmetic or dermatological composition. In this case, it finds its application in a large number of treatments, in particular cosmetic treatments of the skin, including the scalp, the hair, the nails, and/or mucous membranes, in particular for caring for, cleansing, making up and/or sun-protecting the skin and/or mucous membranes.

Thus, the present invention provides for the cosmetic use of the composition as defined above, for treating, protecting, caring for, removing make-up from and/or cleansing the skin, the lips and/or the hair, and/or for making up the skin and/or the lips.

Another aspect of the invention is a cosmetic treatment process for the skin, including the scalp, the hair and/or the lips, characterized in that a composition as defined above is applied to the skin, the hair and/or the lips.

In a known manner, the composition of the invention can also contain adjuvants that are common in cosmetics and/or dermatology, such as active agents, preserving agents, antioxidants, complexing agents, pH modifiers (acids or bases), fragrances, fillers, bactericides, odor absorbers, dyestuffs (pigments and dyes) or lipid vesicles. The amounts of these various adjuvants are those conventionally used in the field under consideration, and, for example, from 0.01 to 20% relative to the total weight of the composition. Depending on their nature, these adjuvants can be introduced into the fatty phase, into the aqueous phase and/or into the lipid vesicles.

Active agents which may be mentioned in particular are moisturizers and, for example, protein hydrolysates and polyols such as glycerol, glycols such as polyethylene glycols, and sugar derivatives.

The active agent(s) can be present, for example, in a concentration ranging from 0.01 to 20%, preferably from 0.1 to 5% and better still from 0.5 to 3%, relative to the total weight of the composition. These ranges for the active agent(s) include all specific values and subranges therebetween, such as 0.02, 0.05, 0.2, 1, 1.5, 2, 5, 10 and 15% by weight relative to the total weight of the composition.

EXAMPLES

Having generally described this invention, a further understanding can be obtained by reference to certain specific examples which are provided herein for purposes of illustration only and are not intended to be limiting unless otherwise specified.

Example 1

| Protective Cream | |
|---|---|
| A. Oily phase | |
| Dimethicone copolyol (DC2-5225C from Dow Corning) | 10% |
| Volatile silicone oil (cyclopentadimethylsiloxane) | 6% |
| Bentone (smectite: Bentone Gel VS-5V from Rheox) | 1% |
| Fluorosilicone oil (fluoropropyl dimethylsiloxane) (X-22-819 from Shin-Etsu) | 4% |
| B. Aqueous phase | |
| Ethanol | 5% |
| Magnesium sulphate | 0.7% |
| Glycerol | 10% |
| Preserving agent | 1% |
| Water | qs 100% |
| Polyamide fibers (Polyamide 0.9 Dtex, 0.3 mm - Paul Bonte company) | 5% |

Procedure: The fibers are introduced into the oily phase without heating and the emulsion is prepared by adding the aqueous phase to the oily phase with vigorous stirring.

A white cream capable of protecting the skin is obtained.

Example 2

| Moisturizing Cream | |
|---|---|
| A. Oily phase | |
| Dimethicone copolyol (DC2-5225C from Dow Corning) | 10% |
| Volatile silicone oil (cyclopentadimethylsiloxane) | 6% |
| Bentone (smectite: Bentone Gel VS-5V from Rheox) | 2.5% |
| Silicone gum (DC 1503 from Dow Corning) | 2.5% |
| Fluorosilicone oil (fluoropropyl dimethylsiloxane) (X-22-819 from Shin-Etsu) | 4% |
| B. Aqueous phase | |
| Ethanol | 5% |
| Magnesium sulphate | 0.7% |
| Glycerol | 10% |
| Preserving agent | 1% |
| Water | qs 100% |
| Polyamide fibers (Polyamide 0.9 Dtex, 0.3 mm - Paul Bonte company) | 5% |

Procedure: The fibers are introduced into the oily phase without heating and the emulsion is prepared by adding the aqueous phase to the oily phase with vigorous stirring.

A white cream capable of moisturizing the skin is obtained.

Example 3

| Foundation | |
|---|---|
| A. Oily phase | |
| Dimethicone copolyol (DC2-5225C from Dow Corning) | 10% |
| Volatile silicone oil (cyclopentadimethylsiloxane) | 6% |
| Dimethicone/vinyl dimethicone crosspolymer and dimethicone KSG 16 from Shi-Etsu) | 4% |
| Bentone (smectite; Bentone Gel VS-5V from Rheox) | 2% |
| Fluorosilicone oil (fluoropropyl dimethylsiloxane) (X-22-819 from Shin-Etsu) | 4% |
| Dyes | 0.02% |
| B. Aqueous phase | |
| Ethanol | 5% |
| Magnesium sulphate | 0.7% |
| Sodium EDTA | 0.1% |
| Glycerol | 5% |
| Preserving agent | 1% |
| Water | qs 100% |
| C. Phase C | |
| Polyamide fibers (Polyamide 0.9 Dtex, 0.3 mm - Paul Bonte company) | 15% |
| Titanium dioxide | 0.9% |
| Iron oxides | 0.2% |

Procedure: Phase C is introduced into the oily phase without heating and is ground, and the emulsion is prepared by adding the aqueous phase to the oily phase with vigorous stirring.

A cream which is capable of giving a healthy appearance is obtained

Obviously, numerous modifications and variations of the present invention are possible in light of the above teachings, It is therefore to be understood that within the scope of the appended claims, the invention may be practiced otherwise than as specifically described herein.

This application is based on French Patent Application Serial No. 99-12910, filed on Oct. 15, 1999, the entire contents of which is incorporated herein by reference.

What is claimed is:

1. A composition in the form of a water-in-oil emulsion, comprising, in a physiologically acceptable medium, an aqueous phase dispersed in an oily phase, fibers, at least one silicone surfactant, and at least one clay, wherein the composition is in the form of a cream and wherein the composition is stable for at least 2 months at 45° C.

2. The composition of claim 1, wherein the fibers are selected from the group consisting of silk, cotton, wool, flax fibers, cellulose fibers, polyamide fibers, rayon fibers, viscose fibers, acetate fibers, poly-p-phenylene terephthamide fibers, acrylic fibers, polyolefin fibers, glass fibers, silica fibers, aramid fibers, carbon fibers, polytetrafluoroethylene fibers, insoluble collagen fibers, polyester fibers, polyvinyl chloride fibers, polyvinylidene chloride fibers, polyvinyl alcohol fibers, polyacrylonitrile fibers, chitosan fibers, polyurethane fibers, polyethylene phthalate fibers, surgical fibers, and mixtures thereof.

3. The composition of claim 1, wherein the fibers are of synthetic origin.

4. The composition of claim 1, wherein the fibers are polyamide fibers or poly-p-phenylene terephthamide fibers.

5. The composition of claim 1, wherein the fibers have a length ranging from 0.1 to 1.5 mm.

6. The composition of claim 1, wherein the fibers have an average diameter ranging from 5 to 50 μm.

7. The composition of claim 1, wherein the fibers are present in an amount ranging from 0.1 to 20% by weight relative to the total weight of the composition.

8. The composition of claim 1, wherein the silicone surfactant is selected from the group consisting of dimethicone copolyols.

9. The composition of claim 1, wherein the amount of silicone surfactant ranges from 0.1 to 5% by weight relative to the total weight of the composition.

10. The composition of claim 1, wherein the clay is one or more clays from a clay family selected from the group consisting of kaolinite, halloysite, dombassite, antigorite, benthierine, pyrophyllite, montmorillonite, beidellite, vermiculite, talc, stevensite, hectorite, saponite, chlorite and sepiolite.

11. The composition of claim 1, wherein the clay is a bentone.

12. The composition of claim 1, wherein the amount of clay ranges from 0.1 to 10% by weight relative to the total weight of the composition.

13. The composition of claim 1, wherein the oily phase is present in an amount ranging from 10 to 50% by weight relative to the total weight of the composition.

14. The composition of claim 1, wherein the oily phase contains at least one silicone oil.

15. The composition of claim 1, which is in the form of a cosmetic or dermatological composition.

16. A method of treating, protecting, caring for, removing make-up from and/or cleansing the skin, the lips and/or the hair, and/or for making up the skin and/or the lips, comprising applying the composition of claim 1 to skin, the lips and/or hair.

17. A method for the cosmetic treatment of the skin, hair and/or lips, comprising applying the composition of claim 1 to the skin, hair and/or lips.

18. The composition of claim 10, wherein the clay from the kaolinite family is selected from the group consisting of kaolinite, dickite and nacrite.

19. The composition of claim 10, wherein the clay is smectite.

20. The composition of claim 10, wherein the clay is one or more clays selected from the group consisting of kaolinite, montmorillonites and hectorites.

21. The composition of claim 1, wherein the clay ranges from 8-10% by weight relative to the total weight of the composition.

* * * * *